United States Patent [19]

Kligman

[11] Patent Number: 5,051,449

[45] Date of Patent: Sep. 24, 1991

[54] TREATMENT OF CELLULITE WITH RETINOIDS

[76] Inventor: Albert M. Kligman, Department of Dermatology University of Pennsylvania Clinical Research Bldg., Room 219, 422 Curie Blvd., Philadelphia, Pa. 19104

[21] Appl. No.: 661,753

[22] Filed: Feb. 27, 1991

[51] Int. Cl.$^5$ ............................................. A61K 31/20
[52] U.S. Cl. .................................... 514/559; 514/381; 514/415; 514/448; 514/461; 514/532; 514/622; 514/725
[58] Field of Search ............... 514/559, 381, 415, 448, 514/461, 532, 622, 725

[56] References Cited

U.S. PATENT DOCUMENTS

| 3,729,568 | 9/1969 | Kligman | 514/559 |
|---|---|---|---|
| 4,288,633 | 9/1981 | Koulbams et al. | 204/232 |
| 4,603,146 | 7/1986 | Kligman | 514/559 |
| 4,877,805 | 10/1989 | Kligman | 514/559 |
| 4,888,342 | 12/1989 | Kligman | 514/559 |

OTHER PUBLICATIONS

Pawson, B. A. et al., "Retinoids at the Threshold: Their Biological Significance and Therapeutic Potential," *Journal of Medicinal Chemistry* 25:1269–1277 (1982)–(Chemical Abstract).

Thomas, J. R. et al., "The Therapeutic Uses of Topical Vitamin A Acid," *Journal of American Academy of Dermatology* 4:505–516 (1981).

*Primary Examiner*—Leonard Schenkman
*Attorney, Agent, or Firm*—Panitch Schwarze Jacobs & Nadel

[57] ABSTRACT

A method for retarding and reversing cellulite comprises topically applying to human skin a retinoid in an amount and for a period of time effective to retard or reverse cellulite where said amount is insufficient to be excessively irritating. The method preferably uses retinoic acid in an emollient vehicle.

15 Claims, No Drawings

TREATMENT OF CELLULITE WITH RETINOIDS

FIELD OF THE INVENTION

The present invention relates to methods of treating cellulite and, more particularly, the present invention is directed to topical treatment of cellulite-afflicted skin using retinoids.

BACKGROUND OF THE INVENTION

Cellulite is a term applied to a skin condition which mainly afflicts post-pubertal women. To some extent, it is a secondary sex characteristic but there is also an associated inflammatory reaction with moderate fibrosis (scarring). Cellulite can occur in any individual but is prominent in heavy set and especially obese women. Cellulite is generally recognized by the dimpled appearance of the skin and is particularly apparent on thick skin, such as the thigh area. This dimpling effect is also commonly called the "mattress phenomenon" because of the periodic dimpling and bulging of the skin resembling a stuffed mattress. Mattressing becomes more apparent when the skin is pinched between the fingers and this "pinch test" may be used as a gross determination of the severity of cellulite.

Histologically, the appearance of cellulite is determined by the sex-linked distribution of female fat. Cellulite appears when subcutaneous or adipose tissue projects upwardly as rounded chambers into the overlying dermis. These locules of fat deeply indent the dermis and approach the surface, creating the mattress phenomenon. In men, the junction between the dermis and subcutaneous tissue is flat without deep extensions of fat into the overlying dermis.

From a cosmetic point of view, cellulite is a source of concern and distress to women. Lumpy-bumpy skin is unpleasant to feel and is often tender. This concern and distress are particularly true among overweight women, among whom more than fifty percent exhibit some degree of cellulite. Large sums of money are spent every year combating this problem. A large array of devices and chemical treatments are used. Conventional physical methods of treating cellulite include electrical stimuli, heat, massage using so-called cellulite gloves, and other mechanical interventions. In addition, many substances, mostly of a botanical origin are touted to control cellulite. These diverse approaches are in use worldwide as home treatments or in numerous spas and salons specializing in cellulite treatment. Some of the pharmacological approaches include caffeine, nicotinates and a host of vasodilators and counter-irritants, such as methyl salicylate.

The long list of therapies is testimony to the lack of beneficial effects from any of these assorted treatments. None have been shown to be effective in reducing cellulite. Only intense exercise and weight loss are modestly beneficial in some cases.

In view of the deficiencies of the prior art methods, it would be desirable to have a method of treating cellulite which is safe, convenient and effective.

Retinoids (e.g. Vitamin A and its derivatives) are known to have a broad spectrum of biological activity. More specifically, these substances affect cell growth, differentiation and proliferation. Vitamin A is essential for maintaining growth and differentiation of epithelial tissues. Retinoids act as a general growth stimulant to many kinds of cells found in skin and elsewhere. They stimulate fibroblasts to make collagen and ground substance, the main constituents of the dermis. Retinoids induce formation of new blood vessels. The metabolic activity of other cell types is also increased. Retinoids have been extensively and effectively used to treat acne vulgaris and a variety of chronic dermatoses, including psoriasis.

Retinoids are being intensively investigated for the prophylaxis of various cancers. They can eradicate actinic keratoses and premalignant tumors arising on photodamaged skin. For a review of developments in retinoid therapy, see Pawson, B.A. et al., "Retinoids at the Threshold: Their Biological Significance and Therapeutic Potential," *Journal of Medicinal Chemistry* 25:1269-1277 (1982). A discussion of retinoids in research and clinical medicine can be found in the publication of a symposium held in Geneva: J.H. Saurat, Editor, "Retinoids: New Trends in Research and Therapy," Karger Publishing Co. (1985).

Certain retinoids, in particular, Vitamin A acid, also known as tretinoin or retinoic acid, have proved to be very effective in acne as set forth in my U.S. Pat. No. 3,729,568. Other topical uses of Vitamin A acid, reviewed by Thomas, J.R. et al., "The Therapeutic Uses of Topical Vitamin A Acid," *Journal of American Academy of Dermatology* 4:505-516 (1981), include treatment of senile comedones, nevus comedonicus, plantar warts, pesudofolliculitis of the beard, keratoacanthoma, solar keratoses, keratosis palmaris et plantaris, Darier's disease, ichthyosis, psoriasis, acanthosis nigricans, lichen planus, molluscum contagiosum, reactive perforating collagenosis, melasma, geographic tongue, Fox-Fordyce disease, cutaneous metastatic melanoma, and keloids or hypertrophic scars.

My U.S. Pat. Nos. 4,603,146; 4,877,805 and 4,888,342 disclose methods for treating sundamaged human skin topically with Vitamin A acid and other retinoids in a vehicle in concentrations not excessively irritating to the skin. Topical retinoic acid causes the skin, particularly human facial skin, to substantially regain and maintain its firmness, turgor and elasticity by stimulating the production of new collagen bundles which comprise the fibrous structural network of skin. Other effects include angiogenesis, increased density of resident dermal cells, such as fibroblasts, mast cells and macrophages. As a result of these various activities, skin which has been badly damaged by sunlight exhibits a great improvement in appearance and in structure. Moreover, some of the ameliorating effects of Vitamin A acid in chronic disorders have been attributed to anti-inflammatory effects.

BRIEF SUMMARY OF THE INVENTION

According to the present invention, a method for retarding and reversing cellulite comprises topically applying to human skin a retinoid in an amount and for a period of time effective to retard and reverse cellulite where the concentration of retinoid is insufficient to be excessively irritating.

In addition, the present invention is directed to a method for preventing recurrence of cellulite in patients in whom the cellulite has been reversed or corrected, comprising topically applying to human skin of the patients a retinoid in an amount and for an indefinite maintenance period effective to prevent cellulite.

The methods of the present invention are preferably performed using retinoic acid in an emollient vehicle.

DETAILED DESCRIPTION OF PREFERRED EMBODIMENTS

Retinoic acid is a derivative of Vitamin A (known in the art as retinol, the alcohol form of Vitamin A). Retinoic acid is the acid metabolite of retinol where the terminal hydroxyl group of retinol is replaced with a carboxyl group. Retinol is formed in the body from beta-carotene, generally found in yellow vegetables, such as carrots. Retinoic acid is available commercially from Johnson & Johnson, sold under the trademark "RETIN-A", for treatment of acne.

Retinoids have been defined as comprising Vitamin A (retinol) and its derivatives, such as Vitamin A aldehyde (retinal) and Vitamin A acid (retinoic acid), comprising the so-called natural retinoids. However, subsequent efforts in synthetic chemistry have resulted in a much larger class of chemical compounds that are termed retinoids due to their biological similarities to Vitamin A and its derivatives.

Compounds useful in the present invention include natural and/or synthetic analogues of Vitamin A which possess the biological activity of Vitamin A acid as described herein. Accordingly, as used herein for purposes of the present invention, the term "retinoid" will be understood to include any of the foregoing compounds. Examples of suitable retinoids for use in the present invention are set forth in Table I, although it will be understood that the invention is not limited thereto.

| Chemical, Common and/or Commercial Name |
| --- |
| Isotretinoin |
| 13-cis-retinoic acid |
| ACCUTANE |
| Etretinate |
| TEGISON |
| (all-E)-9-(4-methoxy-2,3,6-trimethylphenyl)-3,7-dimethyl-2,4,6,8-nonatetraenoic acid ethyl ester |
| Etretin |
| (all-E)-9-(4-methoxy-2,3,6,-trimethylphenyl)-3,7-dimenthyl-2,4,6,8,-nonatetraenoic acid |
| Motretinide |
| N-ethyl-9-(4-methoxy-2,3,6-trimethylphenyl)-3, 7-dimethyl-2,4,6,8-nonatetraenamide |
| (E,E)-9-(2,6-dichloro-4-methoxy-3-methylphenyl)-3,7-dimethyl-2,4,6,8-nonatetraenoid acid ethyl ester |
| 7,8-didehydroretinoic acid |
| (E,E)-4-[2-methyl-4-(2,6,6-trimethyl-1-cyclohexen-1-yl)-1,3-butadienyl]benzoic acid. |
| (E)-4-[4-methyl-6-(2,6,6-trimethyl-1-cyclohexen-1-yl)-1,3,5-hexatrienyl] benzoic acid |
| (all-E)-3,7-dimethyl-9-(3-thienyl)-2,4,6,8-nonatetraenoic acid |
| (E,E,E)-3-methyl-7-(5,6,7,8-tetrahydro-5,5,8,8-tetramethyl-2-naphthalenyl)-2,4,6-octatrienoic acid |
| (E)-6-[2-(2,6,6-trimethyl-1-cyclohexen-1-yl) ethenyl]-2-naphthalenecarboxylic acid |
| (E,E,E)-7-(2,3-dihydro-1,1,3,3-tetramethyl-1H-inden-5-yl)-3-methyl-2,4,6-octatrienoic acid |
| (E)-4-[2,3-dihydro-1,1,3,3-tetramethyl-1H-inden-5-yl)-1-propenyl] benzoic acid |
| TTNPB |
| (E)-4-[2-(5,6,7,8-tetrahydro-5,5,8,8-tetramethyl-2-naphthalenyl-1-propenyl] benzoic acid |
| (E)-4-[2-(5,6,7,8-tetrahydro-3-methyl-5,5,8,8-tetramethyl-2-naphthalenyl)-1-propenyl] benzoic acid |
| (E)-1,2,3,4-tetrahydro-1,1,4,4-tetramethyl-6-(1-methyl-2-phenylethyl) naphthalene |
| 6-(1,2,3,4-tetrahydro-1,1,4,4-tetramethyl-6-naphthyl)-2-naphthalene-carboxylic acid |
| (E)-6-[2-[4-(ethylsulfonyl)phenyl-1-methylethenyl]-1,2,3,4-tetrahydro-1,1,4,4-tetramethylnaphthalene |
| 4-[5,6,7,8-tetrahydro-5,5,8,8-tetramethyl-2-naphthalenyl)ethynyl] benzoic acid |
| (E)-2-(1,1,4,4-tetramethyl-1,2,3,4-tetrahydronaphth-7-yl)-[4-tetrazol-5-yl) phenyl]-1-propene |
| (E)-4-[2-(5,6,7,8-tetrahydro-7-hydroxy-5,5,8,8-tetramethyl-2-naphthalenyl)-1-propenyl] benzyl alcohol |
| AM-80 |
| 2-(4-Carboxybenzamido)-5,6,7,8-tetrahydro-5,5,8,8-tetramethylnaphthalene |
| AM-580 |
| 2-[N-(4-Carboxyphenyl)carbamoyl]-5,6,7,8-tetrahydro-5,5,8,8-tetramethylnaphthalene |
| CH-55 |
| 1-[3,5-(Di-tert-butyl)benzoyl]-2-(4-Carboxyphenyl)ethene |
| TTNT |
| 2-(5,6,7,8-tetrahydro-5,5,8,8-tetramethyl-2-naphthyl)-6-benzo(b) thiophene carboxylic acid |
| TTNF |
| 2-(5,6,7,8-tetrahydro-5,5,8,8-tetramethyl-2-naphthyl)-6-benzo(b) furancarboxylic acid |
| TTNI |
| 2-(5,6,7,8-tetrahydro-5,5,8,8-tetramethyl-2-naphthyl)-6-indolecarboxylic acid |
| TTNN |
| 2-(5,6,7,8-tetrahydro-5,5,8,8-tetramethyl-2-naphthyl)-6-naphthalene carboxylic acid |
| p-(5,6,7,8-tetrahydro-5,5,8,8-tetramethyl-2-anthracenyl) benzoic acid |
| Esters or amides of 13-trans retinoic acid or 13-cis retinoic acid wherein the —OH group of the carboxylic acid (—COOH) group is substituted by —$OR^1$ or $NR^2R^3$, wherein $R^1$, $R^2$ and $R^3$ are such that these esters or amides can be converted to 13-trans retinoic acid or 13-cis retinoic acid through hydrolysis, metabolism, cleavage, etc. |

Also encompassed within the term "retinoid" are geometric and stereoisomers of the retinoids.

Although the method of the present invention applies to the treatment of cellulite using retinoids generally, methods are described below with specific examples using retinoic acid (specifically the commercially available "RETIN-A" preparation). It will be readily appreciated by one skilled in the medical arts that all retinoids bearing a biological similarity to Vitamin A acid and its derivatives may be used in the treatment of cellulite in accordance with the present invention.

Retinoids surprisingly reduce the signs of cellulite when applied topically to human skin, particularly female skin. Mattressing is partially effaced and the skin contour becomes more even. Lumpy-bumpy skin becomes smoother. Topical application may be performed by a number of methods which will be apparent to one skilled in the art of pharmacology. In one embodiment of the present invention, the retinoid is applied to skin affected by cellulite by inunction or any conventional topical applicator device known to those skilled in the art of pharmacology.

The dosage of retinoid (discussed below) required to effectively treat cellulite while avoiding excessive irritation to the skin is surprisingly low. Accordingly, the retinoid should be carried in a non-toxic, dermatologically-acceptable vehicle, preferably a cream, lotion, solution or gel for easy application to the skin. Some retinoids are mild irritants and may cause redness and scaling, which may be accompanied by some tenderness and tightness. These reactions are transient and quickly disappear when application is stopped.

According to a presently preferred embodiment of the present invention, the retinoid is topically applied in an emollient vehicle, which preferably comprises a pharmaceutically acceptable, non-toxic, non-irritating retinoid carrier or solvent appropriate for use on human skin. A presently preferred, commercially available retinoid preparation comprises "RETIN-A" cream (0.05% or 0.1%). Those skilled in the art will understand, however, that other pharmaceutically acceptable emollient vehicles may be used in accordance with the present invention.

In the practice of the present invention, the therapeutically effective concentrations of retinoids are preferably applied in a once or twice daily dosage to the affected areas. Factors such as age, weight, general condition of the skin and extent of cellulite determine the best frequency of application for the individual patient. Application of retinoids may be begun at any stage, although better results can be predicted when applied to less severe cellulite in women whose obesity is only moderate. In addition, exercise and dieting may enhance the therapeutic benefits of the present invention.

The therapeutic effects of the present invention may be maintained once the effects of cellulite have been corrected. A reduced maintenance dosage preferably comprises topical application of the retinoid doses of the present invention twice or thrice weekly. It will be understood by one skilled in the art that a reduced maintenance dosage having fewer or more frequent topical applications weekly may be practiced in accordance with the present invention.

The retinoid is used in accordance with the present invention in a therapeutically effective concentration. As used herein, "therapeutically effective concentration" will be understood as that level of retinoid, which will retard or correct the cellulite. It will be appreciated that the therapeutically effective concentration will depend on the activity of the particular retinoid selected, which can be determined by one skilled in the art based on the present disclosure. For convenience, the amount may be expressed in terms of the equivalent of retinoic acid as the standard.

In accordance with one embodiment of the present invention, it is preferred that the therapeutically effective concentration comprise about 0.01% to about 0.25%, expressed in percent weight retinoic acid equivalents. More preferably, where the retinoid is topically applied in an emollient vehicle, the therapeutically effective concentration of the retinoid is equivalent from about 0.025% to about 0.10% retinoic acid by weight. One skilled in the art will recognize that factors, such as age, weight, general condition of the skin, extent of cellulite and sensitivity to retinoids, will affect the choice of retinoid concentrations used in accordance with the present invention, which may be greater or lower, depending on the individual patient.

The rate and extent of improvement of cellulite according to the present invention may be monitored by techniques and analyses common to the art. Gross clinical analysis, such as the pinch test to determine the extent of mattressing, is perhaps the most convenient and, given the cosmetic nature of cellulite affliction, probably the most relevant method to determine progress. However, other techniques provide useful information. For example, ultrasound instruments can be used non-invasively to determine skin thickness, and the distribution of fat as well as the density of the dermis. Additionally, tissue can be excised and examined microscopically to assess structural changes. I have used both of these methods.

While the inventor does not wish to be bound by any particular theory, it is believed that retinoids alleviate cellulite, particularly the mattressing phenomenon, through a combination of factors, including:

(1) Stimulating fibroblasts to synthesize increased quantities of ground substance (glycoproteins and glycosaminoglycans) in which collagen fibers are suspended and move past each other as the skin stretches. Alone, more ground substance will firm up the skin due to the high hygroscopicity and turgidity of hyaluronic acid. Hyaluronic acid is a major component of the ground substance or mucin, in which the fibers are suspended and responsible mainly for retaining water and keeping the dermis hydrated and turgid.

(2) Increasing the proliferative and metabolic activity of fibroblasts, which results in the deposition of new collagen in the upper dermis. Increased collagen adds bulk and density to the skin.

(3) Stimulating blood flow and promoting the formation of vascular tissues (angiogenesis), which improves circulation, enhancing the activity of the other cell types in the dermis.

(4) Thickening of the epidermis, a result of enhanced proliferation of germinative cells, which also contributes to the physical dimension of the surface layer. Increased physical dimension has the effect of adding firmness to the skin.

No other pharmaceutical agent has these multiple effects, all of which are beneficial to retard and correct cellulite. A firmer, thicker and healthier dermis achieved by applying retinoids in accordance with the present invention inhibits the mobility of easily compressible fat locules, limiting their projection from the subcutaneous fat layer into the overlying dermis.

The invention will now be illustrated in more detail by reference to the following specific, non-limiting examples:

EXAMPLE I

In a series of uncontrolled experiments over the past two years, at least sixty women having visibly apparent indications of cellulite were treated at the Center for Human Appearance in Philadelphia, Pa. Over a period of at least six months for each woman, a retinoic acid preparation ("RETIN-A" 0.05% or 0.010% by weight) was applied to cellulity-afflicated skin (mainly the thigh) by daily rubbing. Application to one thigh was once daily at the start, increased to twice daily within a few weeks. As a control, a non-medicated commercially available "Purpose" cream was applied to the opposite thigh.

In the great majority of the treated women, moderate to marked improvement was observable on the retinoic acid-treated side using the pinch test. The opposite side showed little or no improvement. The women, themselves, noticed amelioration of the cellulite and increased firmness on the retinoic acid-treated side and were highly motivated to continue the therapy. The therapeutic effects of the treatment were maintained by continued application thrice weekly.

EXAMPLE II

In a second uncontrolled experiment, nine women having readily observable cellulite were treated at the Center for Human Appearance as in Example I. Over a period of six months, 0.10% "RETIN-A" cream was applied to cellulite-afflicted thigh skin, once daily at the start and twice daily later, by rubbing the cream on one thigh while "Purpose" cream was applied to the opposite thigh. The creams were massaged over the surface for about 30 seconds each time. At the end of the six months, excision biopsies from each thigh were obtained from each woman. The tissue was embedded in paraffin, sections were cut and stained for examination by light microscopy. The retinoic acid-treated side showed a greatly thickened epidermis and an increased number of new blood vessels using the conventional haemotoxylin and eosin technique. A special stain (Hale) showed increased glycosaminoglycans. Van Gieson's stain showed deeper staining of the collagen bundles, reflecting increased synthesis of collagen. Moreover, a moderate inflammatory reaction in the fibrous septae dividing the fat compartments of the subcutaneous tissue was eliminated on the retinoic acid side. Fibrosis (scarring) was also reduced.

In addition, the retinoic acid-treated and non-treated sides of each woman were examined by B-scan ultrasound. The retinoic acid-treated side appeared thicker, denser and generated more homogeneous echoes in the dermis as compared to the non-treated side. Moreover, ultrasound indicated that fat locules did not project as deeply into the dermis, indicating that these projections were contained by the firmer connective tissue.

The present invention may be embodied in other specific forms without departing from the spirit or essential attributes thereof and, accordingly, reference should be made to the appended claims, rather than to the specification, as indicating to the scope of the invention.

I claim:

1. A method for retarding and reversing cellulite, comprising topically applying to human skin a retinoid in an amount and for a period of time effective to retard and reverse cellulite, said amount being insufficient to be excessively irritating.

2. The method according to claim 1, wherein the retinoid is present in an emollient vehicle.

3. The method according to claim 1, wherein the amount of retinoid is an amount equivalent to about 0.01% to about 0.25% retinoic acid by weight concentration.

4. The method according to claim 2, wherein the amount of retinoid in the emollient vehicle is an amount equivalent to about 0.05% to about 0.1% retinoic acid by weight concentration.

5. The method according to claim 1, wherein the retinoid is applied in a once daily dosage.

6. The method according to claim 1, wherein the retinoid is applied in a twice daily dosage.

7. A method according to claim 1, wherein said retinoid is selected from the group consisting of retinoic acid, retinoic acid derivatives and stereoisomers thereof.

8. A method according to claim 7, wherein said retinoid comprises retinoic acid.

9. A method of preventing recurrence of cellulite in patients in which the effects of cellulite has been retarded and reversed, comprising topically applying to human skin of said patients a retinoid in an amount and for an indefinite maintenance period of time effective to prevent cellulite, said amount being insufficient to be excessively irritating.

10. The method according to claim 9, wherein the retinoid is present in an emollient vehicle.

11. The method according to claim 9, wherein the amount of retinoid is an amount equivalent to about 0.01% to about 0.25% retinoic acid by weight concentration.

12. The method according to claim 10, wherein the amount of retinoid in the emollient vehicle is an amount equivalent to about 0.05% to about 0.1% retinoic acid by weight concentration.

13. A method according to claim 9, wherein said retinoid is selected from the group consisting of retinoic acid, retinoic acid derivatives and stereoisomers thereof.

14. A method according to claim 13, wherein said retinoid comprises retinoic acid.

15. The method according to claim 9, wherein said indefinite maintenance period of time comprises topical application of said retinoid about thrice weekly.

* * * * *